United States Patent [19]
Cook et al.

[11] Patent Number: 5,855,917
[45] Date of Patent: Jan. 5, 1999

[54] METHOD FOR CONTROLLING BODY FAT AND/OR BODY WEIGHT IN ANIMALS AND PHARMACEUTICAL COMPOSITIONS FOR USE THEREIN COMPRISING 20-CARBON CONJUGATED UNSATURATED FATTY ACIDS

[75] Inventors: Mark E. Cook; Yeonhwa Park; Michael W. Pariza, all of Madison, Wis.

[73] Assignee: Wisconsin Alumni Research Foundation, Madison, Wis.

[21] Appl. No.: 759,496

[22] Filed: Dec. 4, 1996

[51] Int. Cl.$^6$ .............................. A61K 9/50; C07C 5/22; C07C 5/23; C07C 5/25
[52] U.S. Cl. .................. 424/502; 424/420; 514/558; 514/560; 585/253; 585/664; 585/671
[58] Field of Search ........................ 435/134; 585/253; 585/664, 671; 424/420, 502; 514/558, 560

[56] References Cited

U.S. PATENT DOCUMENTS

| | | | |
|---|---|---|---|
| 3,291,816 | 12/1966 | Goldblatt et al. | 554/33 |
| 3,645,822 | 2/1972 | Widiger et al. | 156/243 |
| 4,393,049 | 7/1983 | Horrobin | 424/643 |
| 4,560,514 | 12/1985 | Samuelsson et al. | 554/219 |
| 4,761,425 | 8/1988 | Girard et al. | 514/456 |
| 5,079,261 | 1/1992 | Serhan et al. | 514/552 |
| 5,322,780 | 6/1994 | Kawashima et al. | 435/134 |
| 5,376,541 | 12/1994 | Kawashima et al. | 435/136 |
| 5,554,646 | 9/1996 | Cook et al. | 514/560 |
| 5,569,677 | 10/1996 | Daines | 514/570 |

FOREIGN PATENT DOCUMENTS

| | | |
|---|---|---|
| 0404300 | 12/1990 | European Pat. Off. . |
| 3094655 | 4/1991 | Japan . |

OTHER PUBLICATIONS

Fretland et al. Biochem. Pharm. vol. 34 (12), pp. 2103–2107, 1985.
Nugteren et al. Prostaglandins. vol. 33 (3), pp. 403–417, 1987.
Nugteren. Biochim. Biophys. Acta. vol. 210, pp. 171–176, 1970
Beerthuis et al. Recl. Trav. Chim. Pays–Bas. vol. 90 (8), pp. 943–960, Abstract enclosed, 1971.
Labelle et al. Tetrahedron. vol. 46 (18), pp. 6301–6310, 1990.
Verhulst et al. Syst. Appl. Microbiol. vol. 9(1–2), pp. 12–15, 1987
Janssen et al. Biomed. Environ. Mass Spectrom. vol. 15 (1), pp. 1–6, Abstact enclosed, 1988.
Haslett, C. et al., "A Double–Blind Evaluation of Evening Primrose Oil as an Antiobesity Agent," *International Journal of Obesity*, 7:549–553 (1983).
Samsonov et al. Voprosy Pitaniya. No. 5, pp. 21–25, see Abstract, 1993.
Silvis. South African Med. J. vol. 81, pp. 162–166, see Abstract, 1992.
Peter Nilsson–Ehle and Michael C. Shotz, "A stable, radioactive substrate emulsion for assay of lipoprotein lipase", Journal of Lipid Research vol. 17, 1976, 1976, pp. 536–541.
Philip C. Calder, Jane A. Bond, David J. Harvey, Siamon Gordon, and Eric A. Newsholme, "Uptake and incorporation of saturated and unsaturated fatty acids into macrophage lipids and their effect upon Macrophage adhesion and phagocytosis", Biochem. J. (1990) 269, pp. 807–814.
S.F. Chin, W. Liu, J.M. Storkson, Y.L. Ha, and M. W. Pariza, "Dietary Sources of Conjugated Dienoic Isomers of Linoleic Acid, a Newly Recognized Class of Anticarcinogens", Journal of Food Composition and Analysis 5, pp. 185–197 (1992).
Sebastiano Banni, Billy W. Day, Rhobert W. Evans, Francesco P. Corongiu, and Benito Lombardi, "Detection of conjugated diene isomers of linoleic acid in liver lipids of rats fed a choline–devoid diet indicates that the diet does not cause lipoperoxidation", Nutritional Biochemistry 6:281–289, 1995.

*Primary Examiner*—Leon B. Lankford, Jr.
*Assistant Examiner*—Christopher R. Tate
*Attorney, Agent, or Firm*—Quarles & Brady

[57] ABSTRACT

Methods of inhibiting lipoprotein lipase and controlling the body fat and the body weight of an animal employ an effective amount of at least one 20 carbon, conjugated, unsaturated, fatty acid. Pharmaceutical compositions for use in the method are also disclosed. The 20-carbon conjugated fatty acids are selected from an eicosadienoic acid, an eicosatrienoic acid, and an eicosatetraenoic acid. Preferably, the fatty acids are 11,13-eicosadienoic acid; 12,14-eicosadienoic acid; 8,11,13-eicosatrienoic acid; 5,8,11,13-eicosatetraenoic acid; 5,8,12,14-eicosatetraenoic acid, or an ester, salt, or mixture thereof.

3 Claims, No Drawings

METHOD FOR CONTROLLING BODY FAT AND/OR BODY WEIGHT IN ANIMALS AND PHARMACEUTICAL COMPOSITIONS FOR USE THEREIN COMPRISING 20-CARBON CONJUGATED UNSATURATED FATTY ACIDS

CROSS REFERENCE TO RELATED APPLICATIONS

Not applicable

FEDERALLY SPONSORED RESEARCH

Not applicable

FIELD OF THE INVENTION

The present invention generally relates to a method of controlling body fat and/or body weight in an animal. It also relates to pharmaceutical compositions for use in the method.

BACKGROUND OF THE INVENTION

In today's health conscious society there is a great interest in the fat content of food. There is a special concern about the saturated fat content of meat because of its alleged relationship to blood cholesterol. As a result, most consumers would prefer to have meats of lower total and saturated fat content. As a result some meats, such as beef, are declining in popularity. There also is a great interest in dieting and other means of controlling (i.e. reducing and/or maintaining) the body fat and/or body weight of humans.

There is an obvious need for both a safe and effective method of controlling the body fat of animals and for pharmaceutical compositions for use in a method of controlling body fat and/or body weight in humans.

BRIEF SUMMARY OF THE INVENTION

It is an object to disclose a safe and effective method of controlling the body fat and/or body weight of an animal.

It also is an object of the present invention to disclose new pharmaceutical compositions.

We have discovered a method of controlling the body fat and/or body weight in an animal which comprises administering to said animal a safe and effective amount of a 20 carbon, conjugated, unsaturated, fatty acid, such as 11,13-eicosadienoic acid; 12,14-eicosadienoic acid; 8,11,13-eicosatrienoic acid; 8,12,14-eicosatrienoic acid; 5,8,11,13-eicosatetraenoic acid; and 5,8,12,14-eicosatetraenoic acid; an active derivative, such as an ester and a non-toxic salt, thereof; and a mixture thereof. Our method is effective in controlling body fat and/or body weight in both mammals and avian species.

Although not all the details of how the method of the present invention controls body fat and/or body weight are known, we have discovered that the administration of the 20 carbon, conjugated, unsaturated, fatty acids and their active derivatives inhibit adipocyte lipoprotein lipase which is known to be essential for fat accumulation.

We have discovered novel pharmaceutical compositions comprising a pharmaceutical carrier and an the active ingredient, which comprises at least one 20 carbon, conjugated, unsaturated, fatty acid or an active derivative, such as an ester or non-toxic salt, thereof, or a mixture thereof.

It will be apparent to those skilled in the art that the aforementioned objects and other advantages may be achieved by the practice of the present invention.

BRIEF DESCRIPTION OF DRAWINGS

Not applicable

DETAILED DESCRIPTION OF THE INVENTION

The preferred compounds for use in the present invention are the compounds, c11, t13-eicosadienoic acid and t12,c14-eicosadienoic acid. These compounds can be made by the alkaline isomerization of c11,c14-eicosadienoic acid or the alkaline isomerization or enzymatic isomerization of 9,12 octadecadienoic acid followed by the enzymatic elongation of the isomerized products.

The 20 carbon conjugated unsaturated, fatty acids having three and four double bonds (i.e. the eicosatrienoic acids and the eicosatetraenoic acids) can be made either by the alkaline isomerization of c11, c14-eicosadienoic acid followed by the desaturation of the c5 and/or c8 position using desaturase enzyme or by the alkaline isomerization or the enzymatic isomerization of c9, c12 octadienoic acid followed by the enzymatic elongation and desaturation of the isomerized products (ie., c9, t11-octadecadienoic acid or t10, c12 octadecadienoic acid). The desired fatty acid is then isolated from the reaction mixture by conventional means.

In one preferred embodiment of the method of the present invention a safe and effective amount of at least one 20 carbon, conjugated, unsaturated, fatty acid or an active derivative thereof or a mixture thereof, is added to the feed of an animal.

In another embodiment, at least one 20 carbon conjugated unsaturated fatty acid, or an active derivative thereof, or a mixture thereof is administered to the animal as a pharmaceutical composition which contains the 20 carbon, conjugated, unsaturated, fatty acid and a pharmaceutical carrier and optionally other ingredients. The amount of the 20 carbon, conjugated, unsaturated, fatty acid which is to be administered is not critical as long as it is enough to be effective because it is relatively non-toxic.

The practice of the present invention is further illustrated by the examples which follow:

EXAMPLE 1

Preparation of Conjugated Eicosadienoic Acid by Alkali Isomerization

Propylene glycol (100 g) containing 26 g KOH was put into a 4-neck round bottom flask (500 ml). The flask was equipped with a mechanical stirrer, a thermometer, a reflux condenser, and a nitrogen inlet. (The nitrogen introduced was first run through two oxygen traps).

Nitrogen was bubbled through the propylene glycol. The flask was placed in an oil bath and the temperature raised to 180° C.–190° C. and held for 10 minutes.

The flask was removed from the oil bath and up to 50 g 11,14-eicosadienoic acid was added as the mixture was swirled. The flask was placed in the oil bath and maintained at 190° C. for 2 h.

The flask then was removed from the oil bath and cooled to room temperature with cold tap water. Methanol (200 ml) was added. The solution was transferred to a 1-liter separatory funnel and acidified (pH<2) with 250 ml 6N HCl. After dilution with 200 ml water, the mixture of conjugated eicosadienoic acid isomers, which consisted primarily of c11,t13-eicosadienoic acid and t12, c14-eicosadienoic acid, was extracted with 200 ml hexane. The hexane extract was first washed with 30% methanol in water (3×200 ml) and then washed with double distilled water (3×200 ml). Anhydrous sodium sulfate was added to remove water. The hexane was removed under vacuum rotoevaporation. The conjugated eicosadienoic acid was stored under argon at −20° C. and the purity determined by GC/ms analysis.

Similar results are obtained using ethylene glycol and heating at 180° C. to 190° C. for 2 to 3 hours.

EXAMPLE 2

Preparation of Conjugated Eicosadienoic Acid Using Microsomal Fraction

A microsomal fraction was prepared from mouse liver. A liver homogenate was prepared using 1 volume of mouse liver and 3 volumes of (w/v) 0.25M sucrose, 1 mM EDTA, 10 mM Tris Cl (pH 7.4). The mixture was centrifuged at 12,000 g for 15 min. Supernates were centrifuged at 100,000 g for 1 hr and rinsed once. Pellets of the microsomal fraction were resuspended before use. All the foregoing steps were performed at 4° C.

The microsomal fraction was assayed for enzymatic activity using an assay system containing 5 mM ATP, 0.5 mM CoA, 5 mM $MgCl_2$, 0.2 mM malonly CoA, 2 mU acyl CoA synthetase, 2 mM NADPH, 5 mM glutathione, 0.1M potassium phosphate buffer (pH 7.4), 0.8 mM fatty acid-albumin complexes (0.4 mM albumin), and microsomal fraction (1–2 mg as protein). The assay mixture was incubated at 37° C. for 4–24 hours.

The conjugated eicosadienoic acid was prepared by treating conjugated octadecadienoic acid synthesized by enzymatic or alkaline isomerization with the microsomal fraction at 37° C. for 20–24 hours.

The conjugated eicosadienoic acid was extracted from the enzymatic reaction mixture with chloroform:methanol (2:1) after addition of an internal standard (heptadecanoic acid).

EXAMPLE 3

Inhibition of Lipase Activity by Conjugated Eicosadienoic Acid

Conjugated eicosadienoic acid was prepared by the method of Example 1.

3T3-L1 preadipocytes, which were purchased from the American Type Culture Collection, were cultured and differentiated as described by Frost, S. C., and Lane, M. D. (1985) *J. Biol. Chem.*, 260, 2646–2652. Fatty acid-albumin complexes were prepared as previously described by Calder, P. C., Bond, J. A., Harvey, D. J., Gordon, S., and Newsholme, E. A. (1990) Biochem. J., 269, 807–814 with slight modifications. Heparin-releasable lipoprotein lipase (10 U heparin/ml incubation medium) was measured as described by Nilsson-Ehle, P., and Schotz, M. C. (1976) *J. Lipid Res.*, 17, 536–541. Protein was determined using the method described by Lowry, O. H., Rosebrough, N. J., Farr, A. L., and Randall, R. J. (1951) *J. Biol. Chem.*, 193, 265–275. Cells were treated with fatty acid-albumin complexes for 48 hrs. The results which clearly indicated that the lipoprotein lipase was inhibited are shown in Table 1.

TABLE 1

Inhibitory effect of conjugated eicosadienoic (c20:2) acid on lipoprotein lipase activity in 3T3-L1 adipocytes.

| | Lipoprotein Lipase Activity (mU/min/mg protein) |
|---|---|
| Control | 10.65 ± 1.11 |
| c20:2 (100 μM) | 4.84 ± 0.80 |
| c20:2 (200 μM) | 2.66 ± 0.78 |

EXAMPLE 4

Eight pigs (20 kg. body weight) are fed a standard control diet containing 0.5% corn oil and an equal number are fed an identical diet in which 0.5% of the corn oil is replaced by 0.5% of the conjugated eicosadienoic acid mixture. Diet is provided free choice every day until the pigs are 110 kg. in weight. After the feeding period the pigs are sacrificed and the fat, protein, water and ash content of the carcasses is analyzed by proximate analysis and the fat depth estimated using ultrasound. Leanness is determined by measuring the back fat at the 10th rib, measuring the loin eye area and the hot carcass weight. Subjective scoring is used to determine the quality grade (i.e. marbling in the muscle). It is found that the carcasses of the pigs fed the conjugated eicosadienoic acid diet contain less fat than the pigs fed the control diet.

The method of the present invention may take other forms. For example, the 20 carbon, conjugated, unsaturated, fatty acids or their active derivatives can be administered to an animal in a pharmaceutical composition, such as tablets, capsules, solutions or emulsions, which contains a safe and effective dose of the 20 carbon, conjugated, unsaturated, fatty acids or their active derivatives.

The animal feeds and pharmaceutical compositions for use in the method of the present invention are those containing one or more of free 20 carbon, conjugated, unsaturated, fatty acids, such as 11,13-eicosadienoic acid, 12,14-eicosadienoic acid, 8,11,13-eicosatrienoic acid, 8,12,14-eicosatrienoic acid, 5,8,11,13-eicosatetraenoic acid and 5,8,12,14-eicosatetraenoic acid, their active derivatives or mixtures thereof, in combination with a conventional animal feed, human food supplement, or a pharmaceutical diluent.

The term "20 carbon, conjugated, unsaturated, fatty acid" as used herein is intended to include, without limitation, the eicosadienoic acids, eicosatrienoic acids and the eicosatetraenoic acids, their isomers, their active derivatives, such as esters and salts, and mixtures thereof. The non-toxic salts of the free acids may be made by reacting the free acids with a non-toxic base. The esters of the free acids, such as the triglyceride esters, may be made by conventional methods.

The preferred method of synthesizing the conjugated eicosadienoic acids is that described in Example 1. However, the acids may also be prepared from 9,12-octadecadienoic acid by the action of an isomerase from a microorganism (e.g. *Butyrivibrio fibrisolvens*) in combination with a crude, purified or cloned elongase and a desaturase from human or other animal tissue or one expressed by bacteria, yeast or plants.

The exact amount of the active form of the 20 carbon, conjugated, unsaturated, fatty acid to be administered, of course, depends upon the animal, the active form employed, and the route of administration. However, generally it will be an amount ranging from about 0.0001 g/kg about 1 g/kg of the animals body weight.

Generally, the amount of the active form of the 20 carbon, conjugated, unsaturated, fatty acid employed as the active ingredient for a pharmaceutical for humans will range from about 100 parts per million (ppm) to will range from about 100 parts per million (ppm) to about 10,000 ppm of the human's diet. However, the upper limit of the amount to be employed is not critical because these acids are relatively non-toxic. The daily dosage of the active ingredient for both reducing and maintaining body fat and body weight will normally be equal to from about 100 mg to about 20,000 mg of the free acid.

The pharmaceutical compositions of the present invention contain the active ingredient in combination with a pharmaceutical carrier. When the compositions are intended for oral administration the carrier can be one or more solid diluents, such as lactose or starch; if the composition is a capsule or liquid the carrier can be a vegetable oil. When the compositions are solutions or suspensions intended for parenteral administration the preferred carrier will be a liquid suitable for injection.

A representative pharmaceutical tablet has the following formula:

Conjugated Eicosadienoic Acid Mixture of Example 1 (calculated as free acids) 600 mg Microcrystalline cellulose, sodium starch glycolate, corn starch, hydrogenated vegetable oil wax, magnesium stearate and talc added.

The normal daily dosage for reducing body fat would be one to thirty tablets per day.

A representative chewable pharmaceutical wafer has the following formula:

Conjugated Eicosadienoic Acid Mixture of Example 1 (calculated as free acids) 1000 mg Added dextrose, sucrose, talc, stearic acid, mineral oil, salt, and natural and artificial flavorings.

The normal daily dosage is one to twenty tablets a day.

A representative capsule would have the following formula:

Conjugated Eicosadienoic Acid Mixture of Example 1 (calculated as free acids) 600 mg Vegetable oil q.s.a.d. 1000 mg.

The normal daily dosage is one to twenty capsules a day.

It will be readily apparent to those skilled in the art that a number of modifications or changes may be made without departing from the spirit and scope of the present invention. Therefore, the invention is only to be limited by the claims.

We claim:

1. A method of controlling the body fat and body weight of an animal, the method comprising administering to the animal a safe and effective amount of at least one 20 carbon conjugated unsaturated fatty acid selected from the group consisting of 11,13-eicosadienoic acid; 12,14-eicosadienoic acid; 8,11,13-eicosatrienoic acid; 8,12,14-eicosatrienoic acid; 5,8,11,13-eicosatetraenoic acid; 5,8,12,14-eicosatetraenoic acid; an ester thereof; a salt thereof; and a mixture thereof which is effective for reducing or maintaining the body fat and body weight of the animal.

2. The method of claim 1 in which the fatty acid is selected from the group consisting of 11,13-eicosadienoic acid, an active ester thereof, and an active salt thereof.

3. The method of claim 1 in which the fatty acid is selected from the group consisting of 12,14-eicosadienoic acid, an active salt thereof, and an active ester thereof.

* * * * *